United States Patent
Omori et al.

(10) Patent No.: US 9,762,977 B2
(45) Date of Patent: Sep. 12, 2017

(54) TERMINAL DEVICE AND TELEMETRY SYSTEM

(71) Applicant: NIHON KOHDEN CORPORATION, Tokyo (JP)

(72) Inventors: Kiyohiro Omori, Tokyo (JP); Takayoshi Okano, Tokyo (JP); Shiro Murata, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 41 days.

(21) Appl. No.: 14/644,890

(22) Filed: Mar. 11, 2015

(65) Prior Publication Data
US 2015/0271574 A1    Sep. 24, 2015

(30) Foreign Application Priority Data

Mar. 20, 2014  (JP) ................................ 2014-058551
Mar. 31, 2014  (JP) ................................ 2014-071640

(51) Int. Cl.
| G08B 21/00 | (2006.01) |
| H04Q 9/00 | (2006.01) |
| G06F 1/28 | (2006.01) |
| A61B 5/00 | (2006.01) |

(52) U.S. Cl.
CPC ............. *H04Q 9/00* (2013.01); *A61B 5/0015* (2013.01); *G06F 1/28* (2013.01); *A61B 5/0002* (2013.01); *A61B 2560/0204* (2013.01)

(58) Field of Classification Search
CPC .... H04Q 9/00; H04Q 2209/823; G08C 15/06; G08C 17/02; G08C 19/00

USPC ........................................ 340/870.16–870.17
See application file for complete search history.

(56) References Cited

U.S. PATENT DOCUMENTS

| 6,376,931 B1 | 4/2002 | Kim |
| 6,690,366 B1 | 2/2004 | Kitahashi |
| 8,130,094 B2* | 3/2012 | Lu ......................... G06F 19/327 340/3.1 |
| 2001/0027384 A1* | 10/2001 | Schulze ............... A61B 5/0006 702/188 |
| 2010/0063365 A1 | 3/2010 | Pisani et al. |

(Continued)

FOREIGN PATENT DOCUMENTS

| DE | 1 805 444 A1 | 5/1970 |
| EP | 2 392 254 A2 | 12/2011 |

(Continued)

OTHER PUBLICATIONS

The extended European search report for the related European Patent Application No. 15158954.6 dated Jul. 28, 2015.

(Continued)

*Primary Examiner* — Kerri McNally
*Assistant Examiner* — Sharmin Akhter
(74) *Attorney, Agent, or Firm* — Pearne & Gordon LLP

(57) ABSTRACT

A terminal device in which a transmitter transmits biological information and battery state information to a biological information display device, includes a shutdown detector that detects a shutdown state of a battery, and a transmission controller that, when the shutdown detector detects the battery shutdown state, causes the transmitter to transmit the battery state information indicative of shutdown.

5 Claims, 7 Drawing Sheets

(56) References Cited

U.S. PATENT DOCUMENTS

| | | | | |
|---|---|---|---|---|
| 2011/0285520 A1* | 11/2011 | Abe | ................... | B60R 25/1018 340/426.1 |
| 2012/0068855 A1* | 3/2012 | Matsumura | .......... | A61B 5/0006 340/870.02 |
| 2013/0237772 A1 | 9/2013 | Pisani et al. | | |

FOREIGN PATENT DOCUMENTS

| | | |
|---|---|---|
| GB | 2 425 180 A | 10/2006 |
| JP | 5-192304 A | 8/1993 |
| JP | H05-192300 A | 8/1993 |
| JP | 2001-188497 A | 7/2001 |
| JP | 2008-194358 A | 8/2008 |
| JP | 2012-011176 A | 1/2012 |

OTHER PUBLICATIONS

Japanese Office action issued in Patent Application No. JP 2014-071640 dated Jun. 16, 2017.

\* cited by examiner

TERMINAL DEVICE AND TELEMETRY SYSTEM

CROSS REFERENCE TO RELATED APPLICATION

This application is based on Japanese Patent Applications Nos. 2014-058551 filed on Mar. 20, 2014, and 2014-071640 filed Mar. 31, 2014, the contents of which are incorporated herein by reference.

BACKGROUND

The presently disclosed subject matter relates to a terminal device and a telemetry system.

JP-A-5-192304 discloses a telemetry system in which a biological information display device on the receiving side monitors the radio wave state of a terminal device performing transmission, and an alarm generates based on a result of the monitoring.

JP-A-5-192304 discloses also that, in the case where a nurse turns off a power switch of a transmitter, a prediction signal is transmitted to a receiver. When the radio wave is stopped at the receiver after the arrival of the prediction signal, it is determined that the shutdown of the transmitter is caused by regular operation, and the alarm is stopped.

JP-A-2001-188497 discloses that notifications of battery exhaustion, battery detachment, and recovery to the normal voltage when a battery is reattached are performed by using a display device having a memory property.

SUMMARY

In the telemetry system disclosed in JP-A-5-192304, an alarm is stopped, but it is impossible to determine the state of the battery. In the device of JP-A-2001-188497, it is impossible to determine the state of a battery in the transmission side.

An object of the presently disclosed subject matter is to provide a terminal device and telemetry system in which a situation where a shutdown state of a battery occurs in the terminal device can be surely determined in a biological information display device that is on the reception side.

According to an aspect of the presently disclosed subject matter, (1) A terminal device in which a transmitter transmits biological information and battery state information to a biological information display device, includes a shutdown detector that detects a shutdown state of a battery and a transmission controller that, when the shutdown detector detects the battery shutdown state, causes the transmitter to transmit the battery state information indicative of shutdown.

(2) In the terminal device of (1), the shutdown detector detects at least one of turn off due to operation of a power switch and battery detachment.

(3) The terminal device of (1) or (2) further includes a power supply controller that, when the power switch is turned on, immediately supplies a power of the battery to the terminal device, and, when the power switch is turned off, shutdown the supply of the battery power after a predetermined time delay.

(4) A telemetry system includes a terminal device and a biological information display device. The terminal device includes a transmitter which transmits at least biological information and battery state information, a shutdown detector which detects a shutdown state of a battery, and a transmission controller which, when the shutdown detector detects a battery shutdown state, causes the transmitter to transmit the battery state information indicative of shutdown. The biological information display device includes a display controller which receives the biological information transmitted from the terminal device to display the information, and, when the battery state information indicative of shutdown of the battery is received from the terminal device, performs a display indicating shutdown of the battery.

(5) In the telemetry system of (4), the battery state information indicative of the shutdown of the battery is information indicating at least one of turn off due to operation of a power switch, and battery detachment, and the display controller performs displays respectively corresponding to kinds of information.

(6) In the telemetry system of (4) or (5), the biological information display device further includes a radio wave state detector which detects a state of a radio wave transmitted from the terminal device, and the display controller performs a display based on the radio wave state detected by the radio wave state detector.

(7) In the telemetry system of (6), the biological information display device further includes a determination unit which obtains information of a remaining charge amount of the battery from the terminal device, and which determines shutdown of the battery in combination with the information of the remaining charge amount and the radio wave state, and the display controller performs a display indicating shutdown of the battery based on the determination of the determination unit.

According to the presently disclosed subject matter, the biological information display device that is on the reception side can determine a situation where a battery shutdown state occurs in the terminal device. Since at least one of turn off due to operation of the power switch, and detachment of the battery is detected, it is possible to identify whether the battery shutdown state is caused by at least one of turn off due to operation of the power switch and detachment of the battery.

DETAILED DESCRIPTION OF EMBODIMENTS

Figure 1:
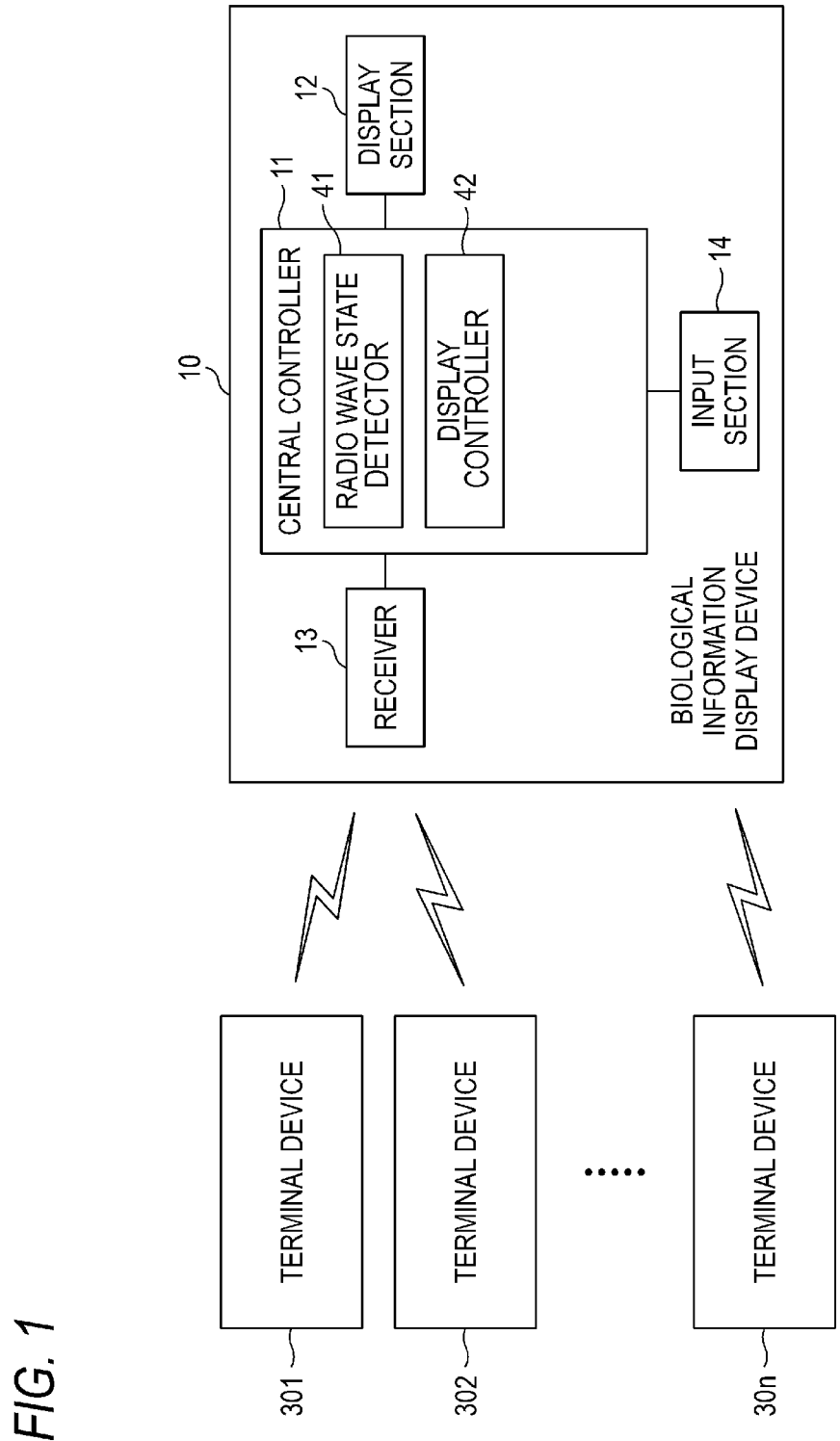
FIG. 1 is a diagram of a telemetry system of an embodiment of the presently disclosed subject matter.

Hereinafter, a terminal device, biological information display device, and telemetry system of an embodiment of the presently disclosed subject matter will be described with reference to the accompanying drawings. In the figures, the identical components are denoted by the same reference numerals, and duplicate description is omitted. FIG. 1 is a diagram of an embodiment of the telemetry system of the presently disclosed subject matter. The telemetry system can include a plurality of terminal devices 301 to 30n which collect and transmit biological information, such as telemeters, and a biological information display device 10 which receives and displays the biological information transmitted from the terminal devices 301 to 30n, such as central monitors. A plurality of biological information display devices 10 may be disposed.

Figure 2:
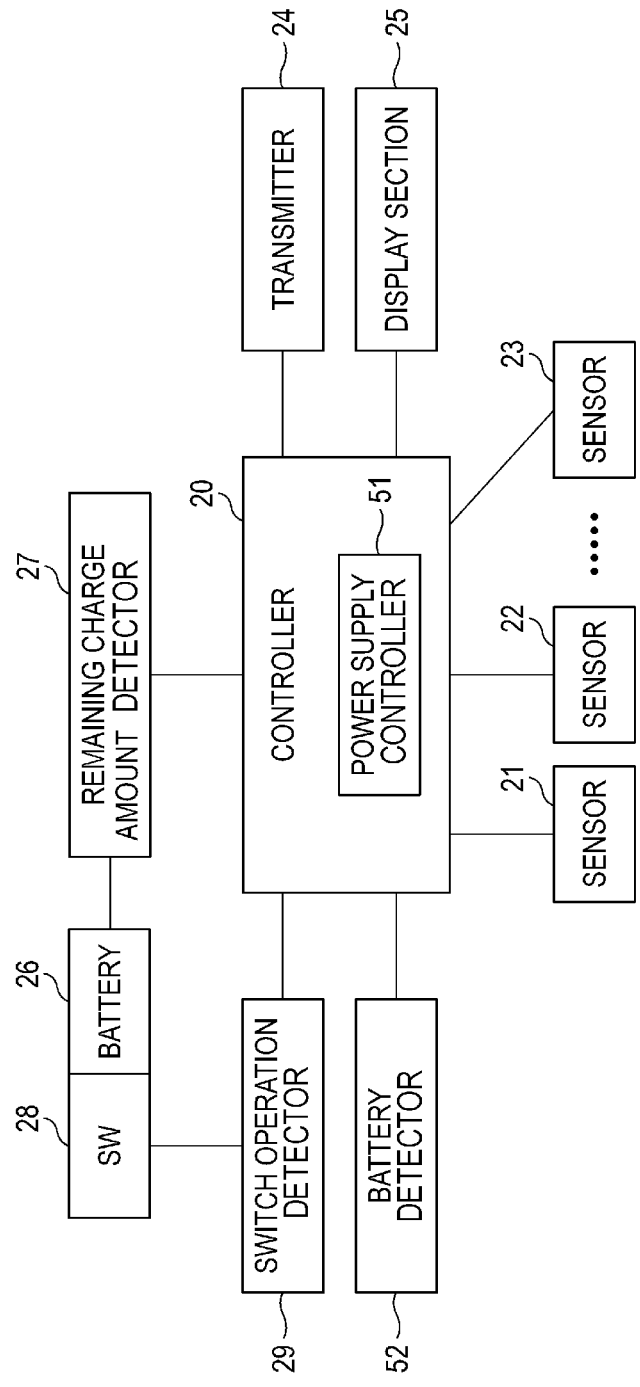
FIG. 2 is a diagram of a terminal device constituting the telemetry system of FIG. 1.

For example, each of the terminal devices 301 to 30n may be configured as shown in FIG. 2. A controller 20 configured by, for example, a computer controls components of each device. A plurality of sensors 21 to 23 are connected to the controller 20. The sensors 21 to 23 measure biological signals such as an electrocardiogram, the blood pressure, brain waves, and the body temperature. The numbers of the sensors in the respective terminal devices 301 to 30n may be different from or equal to one another.

A transmitter 24 is connected to the controller 20. The biological signals obtained from the sensors 21 to 23 are transmitted from the transmitter 24. Moreover, a display section 25 for displaying the operation status of the device and the like is connected to the controller 20.

Each of the terminal devices 301 to 30n operates by power of a battery 26. A remaining charge amount detector 27 is disposed in order to detect the remaining charge amount of the battery 26. Information of the remaining charge amount obtained by the remaining charge amount detector 27 is fetched by the controller 20, and then transmitted from the transmitter 24.

A power switch 28 is disposed in each of the terminal devices 301 to 30n. On/off operations of the power switch 28 are detected by a switch operation detector 29. On/off information of the power switch 28 detected by the switch operation detector 29 is sent to the controller 20. The controller 20 includes a power supply controller 51. The power supply controller 51 receives the on/off information of the power switch 28, and performs controls related to a power supply.

Upon reception of the on information of the power switch 28, the power supply controller 51 immediately starts a power supply from the battery 26 to the components. By contrast, when the power supply controller 51 receives the off information of the power switch 28, the power supply controller 51 stops supplying the power supply from the battery 26 to the components after elapse of a predetermined time period. The controller 20 which is the transmission controller transmits power off information from the transmitter 24 during the predetermined time period.

A battery detector 52 is disposed in each of the terminal devices 301 to 30n. For example, the battery detector 52 can be realized by a configuration where a switch or sensor for detecting a battery is disposed in a battery box. The unit detects a state where the battery 26 is detached from the battery box (hereinafter, the state is referred to as the battery detachment state), and notifies the controller 20 of the state. The controller 20 which is the transmission controller transmits the battery detachment information from the transmitter 24. Each of the terminal devices 301 to 30n may include an another battery for detecting a state of the switch or sensor and transmitting the battery detachment state.

The on/off information of the power switch 28 and the battery detachment state indicate the battery shutdown state, and the switch operation detector 29 and the battery detector 52 constitute the shutdown detector for detecting the shutdown state of the battery. Although the switch operation detector 29 and the battery detector 52 are disposed in the embodiment, only one of these units may be disposed.

The biological information display device 10 can include a central controller 11 configured by, for example, a computer. A display section 12, a receiver 13, and an input section 14 are connected to the central controller 11. The display section 12 displays biological information and the like. The receiver 13 is used for receiving the biological information transmitted from the terminal devices 301 to 30n, and the like. The input section 14 can include a touch panel, a keyboard, a mouse, or the like, and is used for inputting a command and an operation on the screen.

The central controller 11 can include a radio wave state detector 41 and a display controller 42. The radio wave state detector 41 detects the states (for example, electric field strengths) of radio waves transmitted from the terminal devices 301 to 30n. When the battery state information indicating shutdown of a battery is transmitted from one of the terminal devices 301 to 30n, the display controller 42 can perform a display indicating shutdown of the battery. The display controller 42 may divide the screen of the display section 12 into a plurality of display regions, and display sets of biological information transmitted from the terminal devices 301 to 30n in the respective corresponding display regions. A unit for generating an alarm sound may be disposed in the biological information display device 10.

Figure 3:
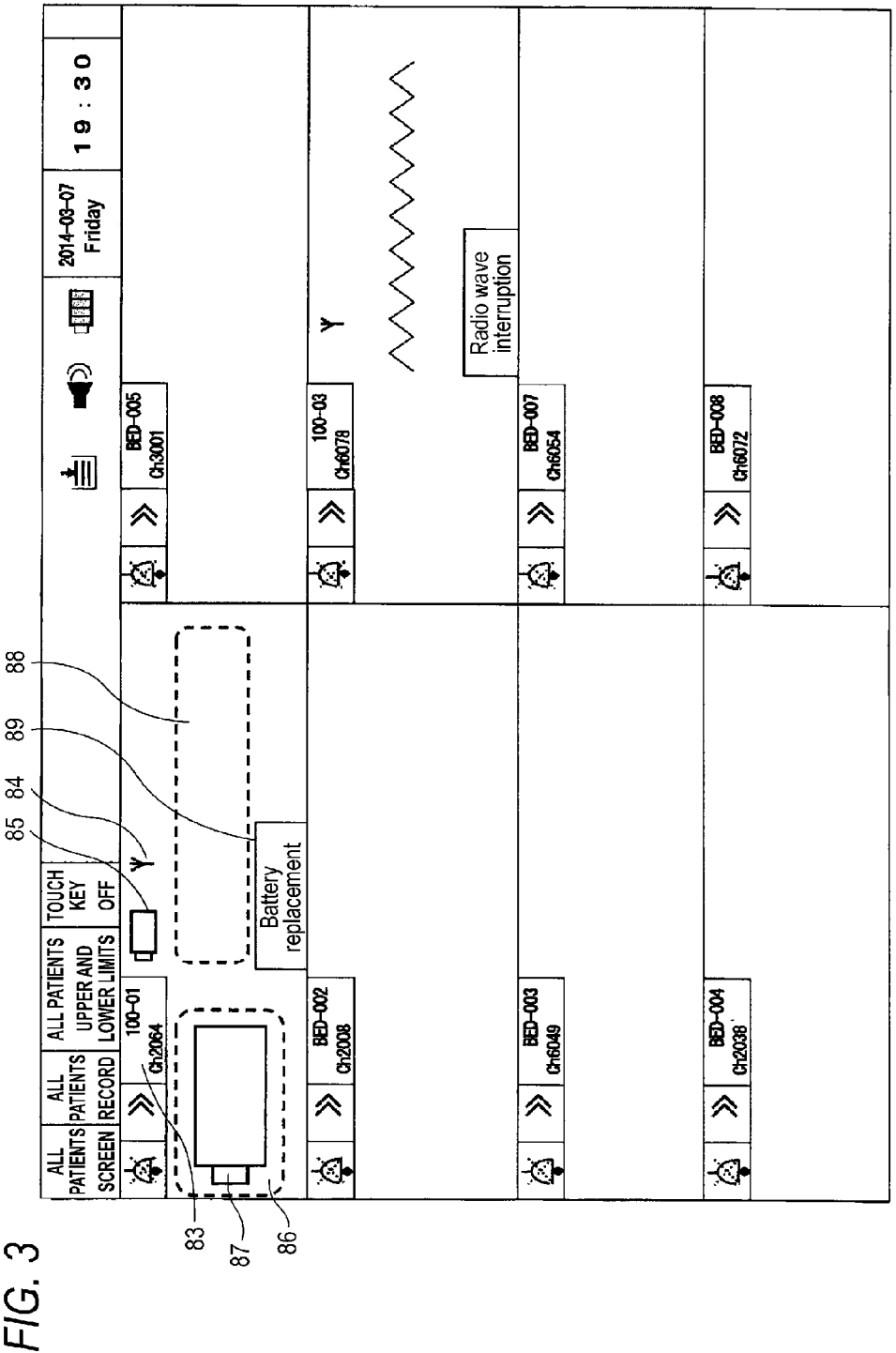
FIG. 3 illustrates a display example of information displayed on one screen of a biological information display device in the embodiment of the presently disclosed subject matter.

FIG. 3 illustrates an example of a display screen in which one screen is divided into regions in accordance with the plurality of terminal devices, and displays respectively relating to sets of information of the terminal devices are performed on the divided display regions. In the example, the whole screen is divided into eight regions in accordance with eight terminal devices to form eight display regions. In a sub display region 83, a patient ID or a bed number is displayed in the upper portion, and a channel number is displayed in the lower portion.

A battery remaining charge amount icon 85 is displayed in a sub display region on the right side of the sub display region 83. As the battery remaining charge amount icon 85, three rectangular segments having a trapezoidal or parallelogram shape are displayed at the maximum in the longitudinal direction in a frame having a shape of a dry cell. The lower the remaining charge amount, the smaller number of segments is displayed.

An antenna icon 84 indicating the reception condition is displayed in a region on the right side of the region where the battery remaining charge amount icon 85 is displayed. As well known in the art, an antenna bar display of the antenna icon 84 is displayed while changing to one of four states in accordance with the reception condition. As the reception condition becomes worse, the number of bars which are displayed in proximity to the right side of the antenna figure display at the leftmost position is further reduced. An alarm battery remaining charge amount icon 87 in which a battery icon indicating that the battery has no remaining charge amount and empty is enlargedly shown is displayed in a sub display region 86 below the region on the left side of the sub display region 83. A sub display region 88 is a display region for displaying biological information, and a signal waveform or the like is displayed in the region. A sub display region 89 is a display region for displaying message characters, and "Battery replacement" which are message characters for prompting battery replacement, "Radio wave interruption" which are message characters indicating interruption of the radio wave, and like are displayed in the region.

Figure 4:
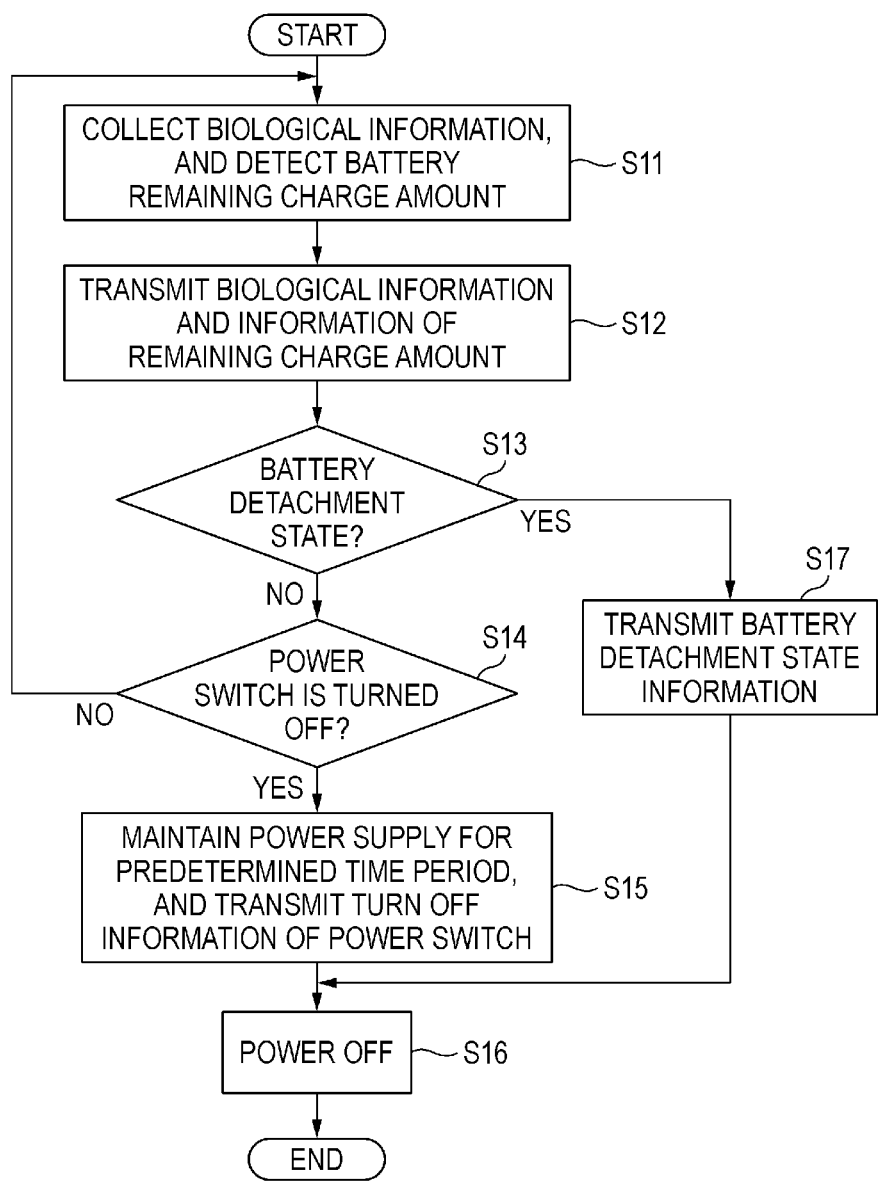
FIG. 4 is a flowchart illustrating the operation of the terminal device of the embodiment of the presently disclosed subject matter.
Figure 5:
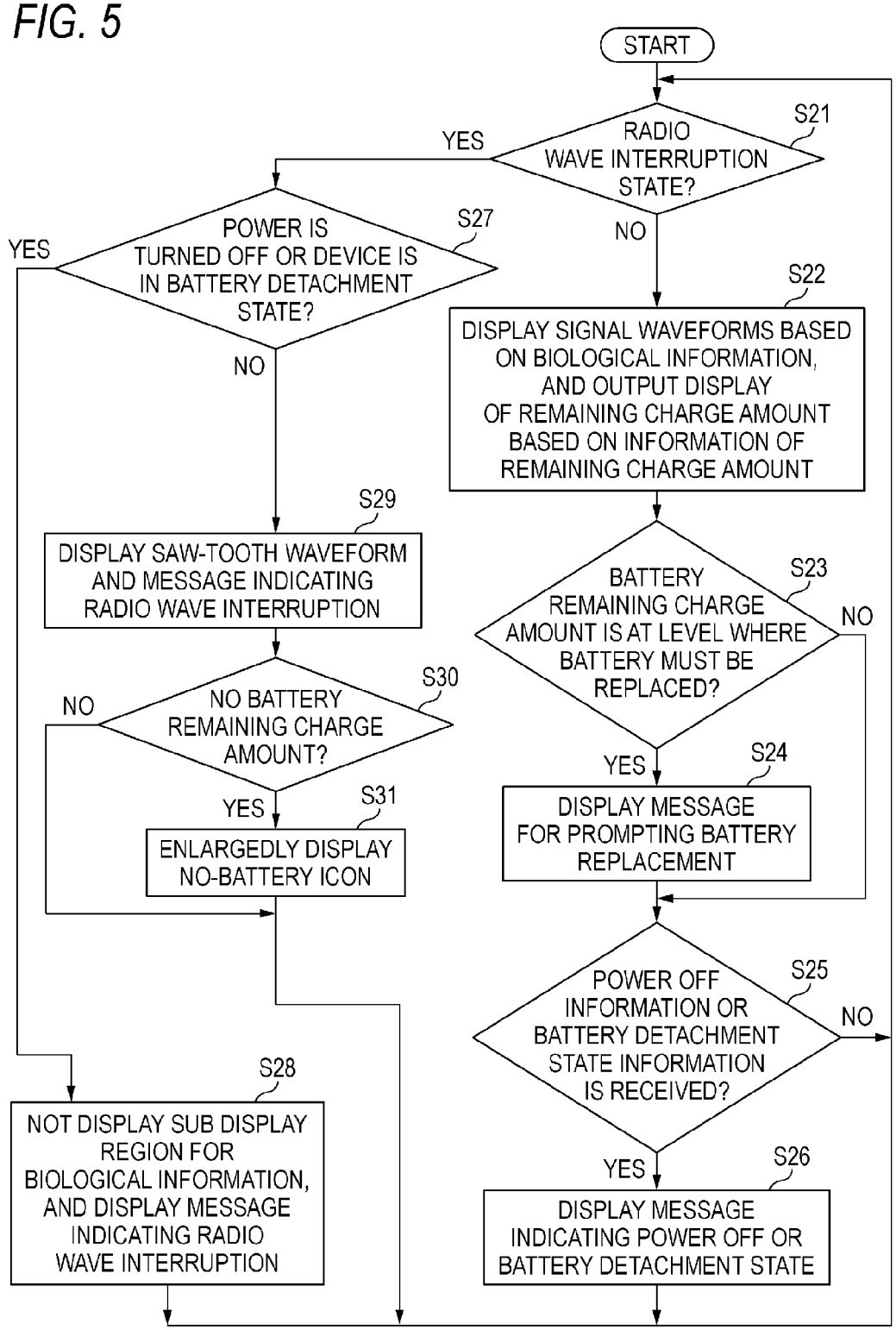
FIG. 5 is a flowchart illustrating the operation of the biological information display device in the embodiment of the presently disclosed subject matter.

In the thus configured telemetry system, for example, the terminal devices 301 to 30*n* operate in accordance with the program shown in FIG. 4. When the central controller 11 of the biological information display device 10 executes a program corresponding to the flowchart shown in FIG. 5, for example, the controller 11 functions as the radio wave state detector 41 and the display controller 42. Hereinafter, the operation will be described with reference to the flowchart. The flowchart of FIG. 5 illustrates the operation corresponding to one terminal device.

In each of the terminal devices 301 to 30*n*, the power switch 28 is turned on, and the operation is started to collect biological information and detect the battery remaining charge amount (S11). Then, the collected biological information and the information of the battery remaining charge amount are transmitted to the biological information display device 10 (S12). Moreover, it is detected whether the device is in the battery detachment state or not (S13). If the device is in the battery detachment state, battery detachment state information is transmitted to the biological information display device 10 (S17), and the device is powered off by detachment of the battery (S16).

If in step S13 the process branches to NO, it is detected whether the power switch 28 is turned off or not (S14). If the power switch 28 is turned off, the power supply is maintained for the predetermined time period, the turn off information of the power switch 28 is transmitted (S15), and the device is powered off after elapse of the predetermined time period (S16).

Figure 6:
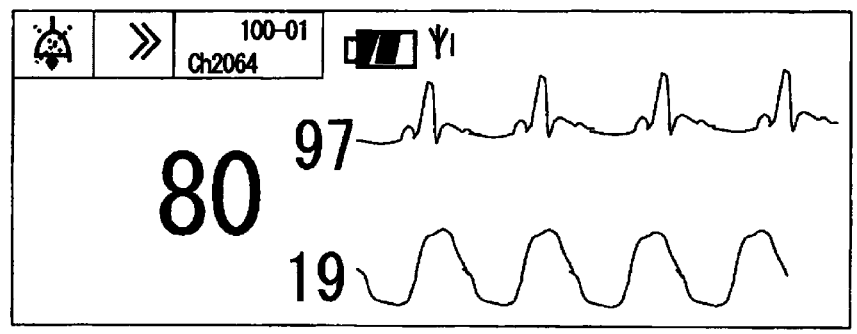
FIG. 6 illustrates a display example of messages and icons displayed by the biological information display device in the embodiment of the presently disclosed subject matter.

In the central controller 11 of the biological information display device 10, by contrast, the power is turned on, and the controller is started to operate as the radio wave state detector 41 and detect whether the radio wave interruption state exists or not (S21). If the process branches to NO, signal waveforms and the like are displayed based on the biological information sent from the terminal devices 301 to 30*n*, and the display of the remaining charge amount is output based on the information of the battery remaining charge amount (S22). FIG. 6 illustrates an example of the display.

Figure 7A:
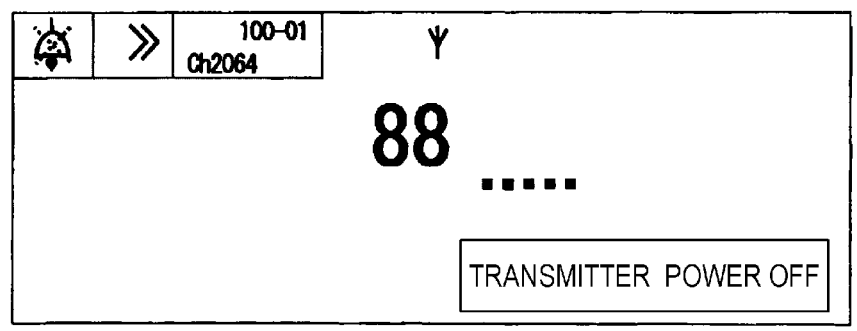
FIGS. 7A and 7B illustrate a display example of messages and icons displayed by the biological information display device in the embodiment of the presently disclosed subject matter.
Figure 7B:
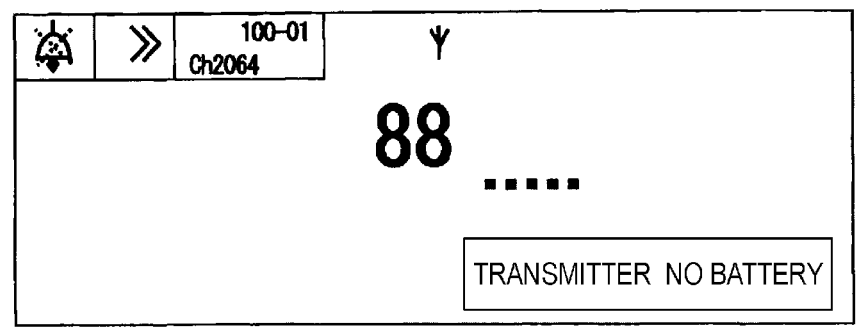

Then, it is detected whether the battery remaining charge amount is at a level where the battery must be replaced or not, based on the battery remaining charge amount information (S23). If the amount is at the level where the battery must be replaced, a message for prompting battery replacement is displayed in the sub display region 89 (S24). After step S24, or if in step S23 the process branches to NO, it is detected whether the power off information or the battery detachment state information is received or not (S25). If in step S25 the process branches to YES, a message indicating the power off or the battery detachment state is displayed in the sub display region 89, based on information sent from the terminal devices 301 to 30*n* (S26). FIG. 7A illustrates an example in which a message indicating the power off is displayed in the sub display region 89, and FIG. 7B illustrates an example in which a message indicating the battery detachment state is displayed in the sub display region 89. In the embodiment, in advance that the radio wave is suddenly lost, as described above, it is clearly known that the operation of turning off the power or that of opening the battery cover is performed on the side of a terminal device, and therefore the medical person can adequately take an subsequent countermeasure.

Figure 8:
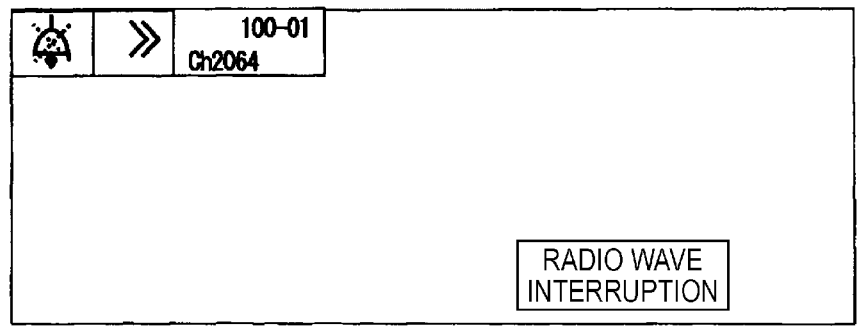
FIG. 8 illustrates a display example of messages and icons displayed by the biological information display device in the embodiment of the presently disclosed subject matter.

If in step S25 the process branches to NO, by contrast, the process returns to step S21 to be continued. If in step S21 the process branches to YES, it is detected whether the power is turned off or the device is in the battery detachment state (S27). If in step S27 the process branches to YES, the display in the sub display region for biological information is not performed, and a message indicating the radio wave interruption is displayed as shown in FIG. 8 (S28).

Figure 9:
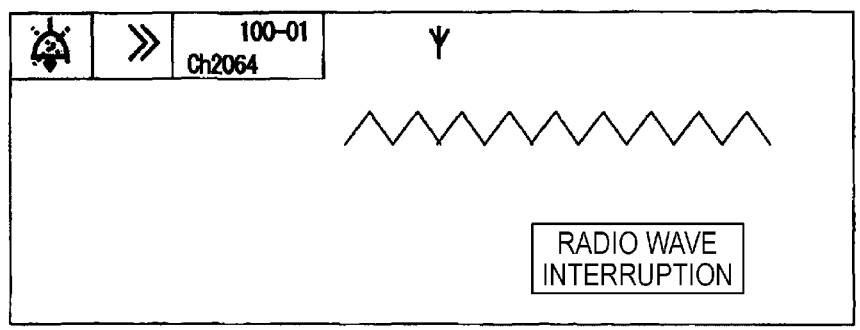
FIG. 9 illustrates a display example of messages and icons displayed by the biological information display device in the embodiment of the presently disclosed subject matter.
Figure 10:
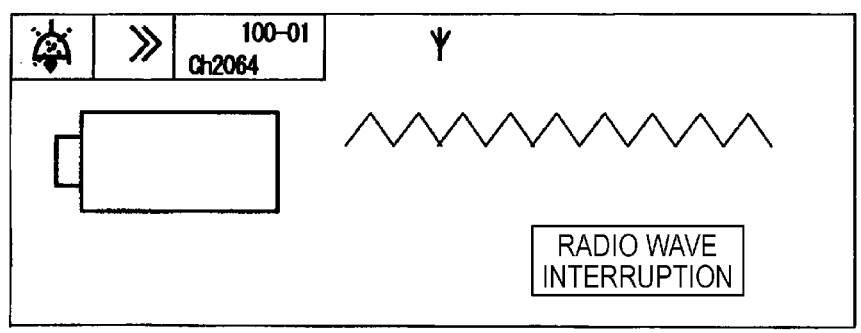
FIG. 10 illustrates a display example of messages and icons displayed by the biological information display device in the embodiment of the presently disclosed subject matter.

If in step S27 the process branches to NO, a saw-tooth waveform and a message indicating the radio wave interruption are displayed as shown in FIG. 9 (S29). In step S29, an audible alarm may be generated. In succession to step S29, it is determined whether a state where the battery has no remaining charge amount is produced or not (S30). If it is determined that the battery has no remaining charge amount, a no-battery icon is enlargedly displayed in the sub display region 86 as shown in FIG. 10 (S31). In step S31, an escalation alarm in which the volume of the audible alarm is increased may be generated. If in step S30 the process branches to NO, the display of the saw-tooth waveform and message indicating the radio wave interruption which have been displayed in step S29 is maintained.

In the embodiment, in the battery shutdown state in which the power is turned off or the battery is detached, as described above, the cause of the shutdown or the like is displayed before the radio wave interruption occurs (FIG. 7), and, after the radio wave interruption, the display (FIG. 8) is performed which is different from displays (FIG. 9) performed in the case where the terminal devices 301 to 30*n* leave the communication range, and where the reception condition is deteriorated. Usually, therefore, it is possible to determine that the radio wave interruption is caused by the power off due to an operation performed by the medical person, or the battery detachment state, and hence it is not required to take unnecessary countermeasures such as that a patient who may leave the communication range is searched, and that the terminal devices 301 to 30*n* are checked for abnormalities. In a case such as that it is forgotten to turn on the power or attach a battery, the display is different from displays performed in the case of out of communication range and deterioration of the reception condition, and it is possible to check also forgetting of turning on of the power and attachment of a battery.

In the embodiment, a shutdown state of a battery is detected based on the power off information or the battery detachment state information. Alternatively, the biological information display device 10 may further include a determination unit which obtains information of the remaining charge amount of the battery from the terminal devices 301 to 30*n*, and which, in combination of the information and the radio wave state, determines shutdown of the battery. In the case where the remaining charge amount of the battery is sufficient, when the radio wave interruption suddenly occurs, for example, it is determined that a battery shutdown state occurs, and the display which is different from displays performed in the case of out of communication range and deterioration of the reception condition can be performed.

What is claimed is:

1. A terminal device in which a transmitter transmits biological information and battery state information to a biological information display device, the terminal device comprising:
   a shutdown detector that detects a shutdown state of a first battery from at least one of an operation of a power switch to turn off the terminal device and detachment of the first battery from the terminal device;
   a transmission controller that, when the shutdown detector detects the first battery shutdown state, causes the transmitter to transmit the first battery state information indicative of shutdown; and
   a second battery that provides power for detecting the shutdown state and transmitting the first battery state information when the first battery is detached.

2. The terminal device according to claim 1 further comprising:
   a power supply controller that, when the power switch is turned on, immediately supplies a power of the first battery to the terminal device, and, when the power switch is turned off, shutdown the supply of the first battery power after a predetermined time delay.

3. The terminal device according to claim 1, wherein the shutdown detector detects the shutdown state of the first battery from detachment of the first battery from the terminal device.

4. A telemetry system comprising:
   a terminal device that includes:
      a transmitter which transmits at least biological information and battery state information;
      a shutdown detector which detects a shutdown state of a battery; and
      a transmission controller which, when the shutdown detector detects a battery shutdown state, causes the transmitter to transmit the battery state information indicative of shutdown; and
   a biological information display device that includes a display controller which receives the biological information transmitted from the terminal device to display the information, and, when the battery state information indicative of shutdown of the battery is received from the terminal device, performs a display indicating shutdown of the battery,
   wherein the biological information display device further includes a radio wave state detector which detects a state of a radio wave transmitted from the terminal device, and the display controller performs a display based on the radio wave state detected by the radio wave state detector, and
   wherein the biological information display device further includes a determination unit which obtains information of a remaining charge amount of the battery from the terminal device, and which determines shutdown of the battery in combination with the information of the remaining charge amount and the radio wave state, and the display controller performs a display indicating shutdown of the battery based on the determination of the determination unit.

5. A telemetry system comprising:
   a terminal device that includes:
      a transmitter which transmits at least biological information and battery state information;
      a shutdown detector which detects a shutdown state of a battery; and
      a transmission controller which, when the shutdown detector detects a battery shutdown state, causes the transmitter to transmit the battery state information indicative of shutdown; and
   a biological information display device that includes a display controller which receives the biological information transmitted from the terminal device to display the information, and, when the battery state information indicative of shutdown of the battery is received from the terminal device, performs a display indicating shutdown of the battery,
   wherein the battery state information indicative of the shutdown of the battery is information indicating at least one of turn off due to operation of a power switch, and battery detachment, and the display controller displays respectively corresponding to kinds of information,
   wherein the biological information display device further includes a radio wave state detector which detects a state of a radio wave transmitted from the terminal device, and the display controller performs a display based on the radio wave state detected by the radio wave state detector, and
   wherein the biological information display device further includes a determination unit which obtains information of a remaining charge amount of the battery from the terminal device, and which determines shutdown of the battery in combination with the information of the remaining charge amount and the radio wave state, and the display controller performs a display indicating shutdown of the battery based on the determination of the determination unit.

* * * * *